United States Patent [19]

Suzuki

[11] 4,399,702
[45] Aug. 23, 1983

[54] METHOD OF MEASURING STRESS DISTRIBUTION IN A SOLID BODY

[75] Inventor: Katsumichi Suzuki, Mito, Japan

[73] Assignee: Hitachi, Ltd., Tokyo, Japan

[21] Appl. No.: 324,443

[22] Filed: Nov. 24, 1981

[30] Foreign Application Priority Data

Nov. 25, 1980 [JP] Japan ................................ 55/164604

[51] Int. Cl.³ ..................... G01N 29/00; G01N 24/04; G01H 5/00
[52] U.S. Cl. ........................................ 73/597; 73/628; 73/624; 73/641
[58] Field of Search ................. 73/597, 624, 625, 628, 73/641

[56] References Cited

U.S. PATENT DOCUMENTS 3,587,297 6/1971 Kammer ................................ 73/597
3,771,355 11/1973 Sachs ...................................... 73/597
3,812,709 5/1974 Benson et al. ......................... 73/597
4,033,182 7/1977 Clotfelter ............................... 73/597

FOREIGN PATENT DOCUMENTS 681366 8/1979 U.S.S.R. ................................. 73/597

*Primary Examiner*—Stephen A. Kreitman
*Assistant Examiner*—David V. Carlson
*Attorney, Agent, or Firm*—Antonelli, Terry & Wands

[57] ABSTRACT

Two ultrasonic wave beams of different frequencies are emitted into a body under consideration from different locations on a surface of the body and a scattered wave beam created at a scattering point in the body by the interaction between the two ultrasonic wave beams is received. The emitting locations of the ultrasonic wave beams and the receiving location of the scattered wave beam are caused to scan. Thus, the stress distribution in the body is measured on the basis of the received outputs resulting from the scanning.

1 Claim, 9 Drawing Figures

METHOD OF MEASURING STRESS DISTRIBUTION IN A SOLID BODY

This invention relates to a method of measuring stress distribution in a solid body such as metals from the velocities of ultrasonic waves.

The relation between the velocity of sound and the stress is analyzed theoretically (see D. S. Hughens et al.: "Second-Order Elastic Deformation of Solids", Physical Review, Vol. 92, No. 5, Dec. 1, 1953, pp. 1145-1149). With a longitudinal wave, for example, $$\rho_o V_l^2 = \lambda + 2\mu - (P/3K_o)(7\lambda + 10\mu + 6l + 4m) \quad (1)$$

stands, where
- $\rho_o$: density
- $V_l$: velocity of longitudinal wave
- $\lambda, \mu$: elastic constants of Lame
- l, m, n: elastic constants of Murnaghan
- P: unidirectional tension
- $K_o = \frac{1}{3}(3\lambda + 2\mu)$: modulus of elasticity of volume.

Let $V_{ol}$ be the velocity of sound under no stress conditions and $\Delta V_l$ a change in the velocity of sound attributable to stress, and the velocity of sound $V_l$ is, $$V_l = V_{ol}(1 + \Delta V_l/V_{ol}) \quad (2)$$

Since $\Delta V_l/V_{ol}$ is very small (0.01 to 0.1%), $$V_l^2 = V_{ol}^2(1 + 2\Delta V_l/V_{ol}) \quad (2)'$$

is obtained. By combining equations (2)' and (1)

$$\Delta V_l/V_{ol} = 1/2\rho_o V_{ol}^2[\lambda + 2\mu - (P/3K_o)(7\lambda + 10\mu + 6l + 4m)] - \tfrac{1}{2} \quad (3)$$

is obtained, indicating that $\Delta V_l/V_{ol}$ is proportional to P. In this manner, stress can be measured by measuring $\Delta V_l/V_{ol}$.

Conventionally, based on the above-described method, distribution of changes in the velocity of sound is measured to determine stress distribution. More specifically, an ultrasonic wave is transmitted from a transmitting sensor to a solid body under the application of a stress and the wave transmitted through the solid body is received by an opposed receiving sensor to measure the propagation time of the wave. Then, the transmitting and receiving sensors are parallely moved by a predetermined distance and the propagation time of an ultrasonic wave at that location is measured. Such a measurement is carried out over a given range of area in which the body exists. Subsequently, the transmitting and receiving sensors are rotated by a predetermined angle as a whole and the above measurement is repeated while this angular or directional relation is maintained. Thus, the propagation times in all-round directions in the body are measured.

Thereafter, distribution of velocities of sound is calculated from the measured values. To this end, an area including the body is divided into cells of a mesh pattern. The cells are numbered by 1, 2, 3, . . . , j, . . . . Let a distance be $L_{ij}$ by which an i-th beam traverses a j-th cell, and the distance $L_{ij}$ can be measured since a relative angle of the i-th beam (or the rotation angle of the transmitting and receiving sensors) is known. It is now assumed that within each cell, the velocity of sound is constant and has a value of $V_j$. Then, the propagation time $T_i$ for the i-th beam is obtained by adding $L_{ij}/V_j$. Namely, $$T_i = \sum_j \frac{L_{ij}}{V_j} + \frac{1}{V_w}(L - \sum_j L_{ij}) \quad (4)$$

is held, where
- $V_w$: velocity of sound in water (underwater body is assumed)
- L: distance between transmitting and receiving sensors.

Equation (4) sets up simultaneous equations of the unknown $V_j$. When at least $V_j$ values are measured of the $T_i$, the unknown $V_j$ can be obtained from equation (4) so that the distribution of velocities of sound can be measured.

This transmission method is, however, unsuitable for practical non-destructive measurement. A reflection method has therefore been proposed which will be described below. According to the reflection method, an ultrasonic wave transmitted from a transmitting sensor is once reflected at a bottom surface of a body, and the reflected wave having a predetermined reflection angle between the transmitted and reflected waves is received by a receiving sensor. While the predetermined reflection angle is kept constant, each sensor is scanned so that the propagation time is measured for each scan. Subsequently, the scanning is carried out to provide a different or second reflection angle. Thus, the $T_i$ corresponding to equation (4) can be measured.

Of the above methods, the former requires beforehand accurate determination of the size of the body and the latter requires beforehand accurate determination of the thickness of the body. Especially, when the thickness of the body is not uniform and the unevenness cannot be detected from the sensor side (this condition exactly corresponds to ordinary inspection), it is impossible for the latter method to measure the velocity of sound and hence the stress distribution.

An object of this invention is to provide a stress distribution measuring method which can obviate the above conventional drawbacks and eliminate the necessity of information regarding thickness and size of a body.

According to this invention, a reference point for non-destructive measurement of velocities of sound is established within a body to ensure the elimination of the information regarding thickness and size of the body. The establishment of the reference point eliminates the necessity of calculation of the aforementioned $L_{ij}$.

This invention will now be explained referring to the accompanying drawings, in which.

Figure 1:
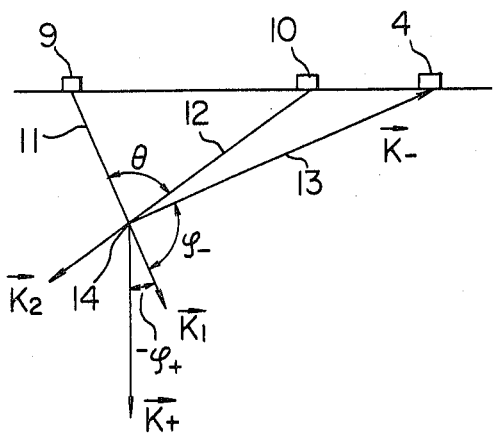
FIG. 1 is a diagrammatic representation showing the principle of scattering created by interaction between two ultrasonic wave beams.

The principle of scattering created by interaction between two ultrasonic wave beams will first be described. When an incident ultrasonic wave collides with another incident ultrasonic wave under predetermined conditions, there are generated a scattered ultrasonic wave of a frequency corresponding to the sum of frequencies of the incident ultrasonic waves and another scattered ultrasonic wave of a frequency corresponding to the difference between frequencies of the incident ultrasonic waves (see J. D. Childress et al.: "Interactions Between Elastic Waves in an Isotropic Solid", Physical Review, Vol. 136, No. 2A, Oct. 19, 1964, pp. A411–A418). As shown in FIG. 1, when transmitting sensors 9 and 10 respectively transmit ultrasonic wave beams 11 and 12 of wave number vectors $\vec{K}_1$ and $\vec{K}_2$ and frequencies $\omega_1$ and $\omega_2$ with an angle $\theta$ therebetween, the two incident ultrasonic waves interact with each other at a crossing 14 to create scattered ultrasonic waves having wave number vectors of $\vec{K}_\pm = \vec{K}_1 \pm \vec{K}_2$ and frequencies of $\omega_\pm = \omega_1 \pm \omega_2$ in directions subtending angles $\psi_\pm$ with respect to the wave number vector $\vec{K}_1$, where $\psi$ is positive in the counterclockwise direction and suffix $\pm$ is reduced to "+" for the scattered ultrasonic wave of the sum frequency and "−" for the scattered ultrasonic wave of the differential frequency. The angle $\theta$ between the incident ultrasonic waves is given by, $$\cos\theta = C_\pm^{-2} \{C_1C_2 \pm \tfrac{1}{2}[C_2\omega_1(C_1\omega_2)^{-1}(C_1^2 - C_\pm^2) + C_1\omega_2(C_2\omega_1)^{-1}(C_2^2 - C_\pm^2)]\} \quad (5)$$

where C is the velocity of sound. The angle $\psi_\pm$ for the scattered ultrasonic waves from the crossing 14 is given by, $$\sin\psi_\pm = \pm C_\pm \omega_2 [C_2(\omega_1 \pm \omega_2)]^{-1} \sin\theta \quad (6)$$

Figure 2:
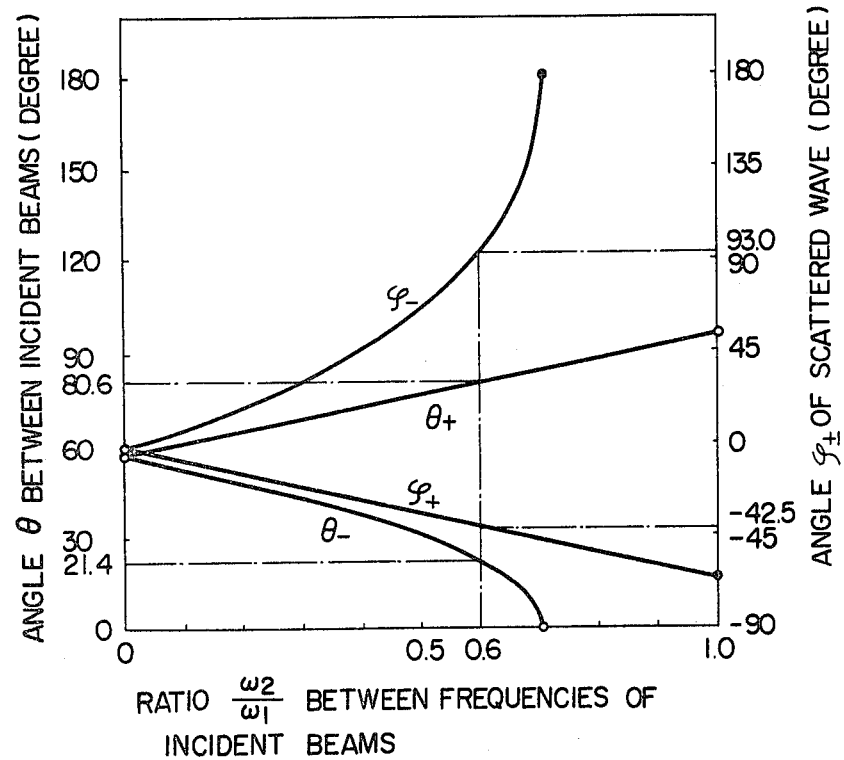
FIG. 2 is a graph showing the angle $\theta$ between incident ultrasonic waves and the angle $\psi_\pm$ between scattered waves with respect to the ratio between frequencies of incident ultrasonic wave beams.

When considering the interaction in a solid body, the incident wave and the scattered wave take the form of either a longitudinal wave or a transversal wave. Assuming that the incident ultrasonic wave beam 11 is a longitudinal wave and the incident ultrasonic wave beam 12 is a transversal wave, the resulting scattered waves are longitudinal waves of the sum frequency and the differential frequency. In this case, the $\theta$ and $\psi_\pm$ are related to $\omega_2/\psi_1$ as shown in FIG. 2.

For example, with an incident longitudinal wave ($\omega_1 = 5$ MHz) and an incident transversal wave ($\omega_2 = 3$ MHz), $\omega_2/\omega_1 = 0.6$ stands. Then, from FIG. 2, the angle $\theta$ between the incident waves is 80.6° for the sum frequency and 21.4° for the differential frequency. The scattered wave 13 involves for the sum frequency, a longitudinal wave of a frequency $\omega_+$ of 8 MHz propagating in a direction as defined by $\psi_+ = -42.5°$ and for the differential frequency, a longitudinal wave of a frequency $\omega_-$ of 2 MHz propagating in a direction as defined by $\psi_- = 93.0°$.

The scattering point 14 of the ultrasonic wave interaction is taken as a reference point for measuring the velocity of sound and used for measuring the sound velocity distribution in the present invention, the principle of which will be described below.

Figure 3:
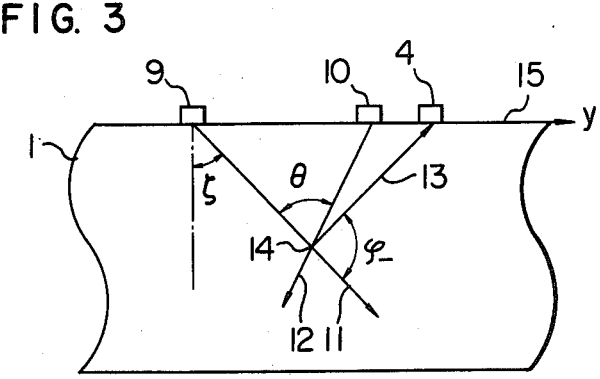
FIGS. 3 and 4 are diagrammatic representations useful in explaining the principle of this invention.

The sensors are arranged and the ultrasonic wave beams propagate as shown in FIG. 3, where $\zeta$ represents the incident angle of an ultrasonic wave beam 11 to a body 1, and other characters are the same as those in FIG. 1.

Figure 4:
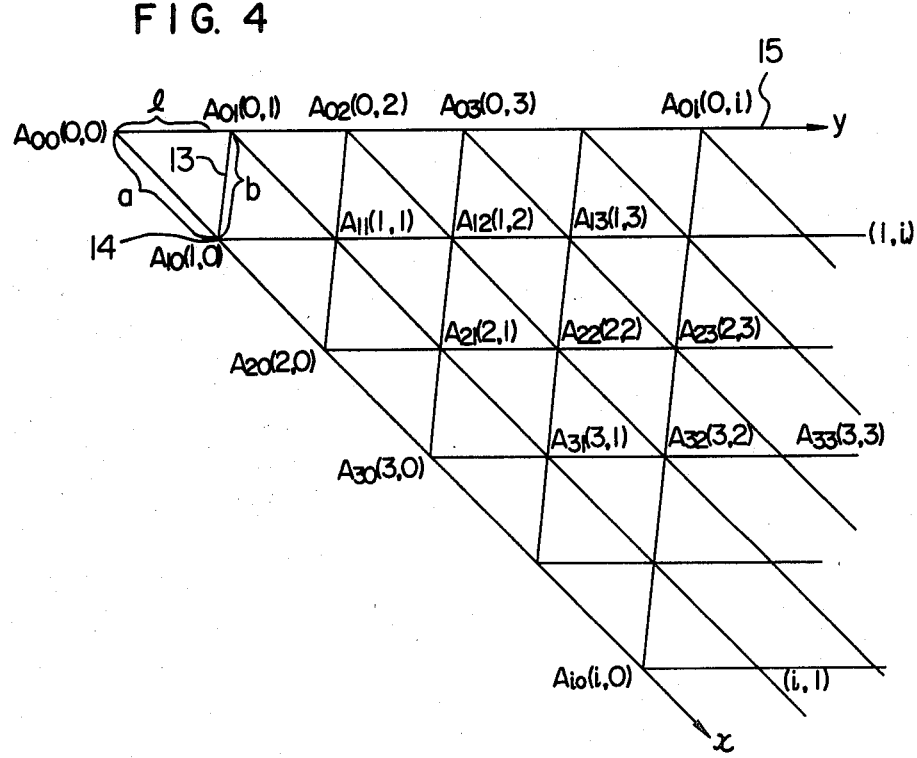

FIG. 4 illustrates an oblique coordinate system wherein a y-axis runs along a surface 15 of the body 1 shown in FIG. 3 and an x-axis extends in a direction in which the ultrasonic wave beam 11 transmitted from a transmitting sensor 9 propagates. When the transmitting sensor 9 is located at a point $A_{00}$ (0, 0), for example, the scattering is then effected at a point $A_{10}$ (1, 0), and a scattered wave 13 is received by a receiving sensor 4 located at a point $A_{01}$ (0, 1). For simplicity of illustration, another transmitting sensor 10 as shown in FIG. 3 is not depicted in FIG. 4.

Now, the transmitting sensor 9 is fixed at the point $A_{00}$ (0, 0) and the receiving sensor 4 initially located at the point $A_{01}$ (0, 1) is moved along the y-axis in sequence of $A_{02}$ (0, 2), $A_{03}$ (0, 3).... Concurrently with the movement of the receiving sensor, the transmitting sensor 10 is also moved while keeping the angle $\theta$ fixed. Then, the scattering point initially located at the point $A_{10}$ (1, 0) is moved along the x-axis in sequence of $A_{20}$ (2, 0), $A_{30}$ (3, 0) .... Subsequently, the transmitting sensor 9 is shifted to the point $A_{01}$ (0, 1) and fixed thereat. Then, as in precedence, the receiving sensor 4 is moved so that the scattering point created at a point $A_{11}$ (1, 1) is moved in sequence of $A_{21}$ (2, 1), $A_{31}$ (3, 1) .... In this manner, the probes are moved to cover the entire area involved in the measurement.

Let a distance between the point $A_{00}$ (0, 0) and the point $A_{10}$ (1, 0) be a and a distance between the point $A_{10}$ (1, 0) and the point $A_{01}$ (0, 1) be b. This denotation of the distances is valid for the remaining triangles. Values of the distances a and b are expressed as.

$$\left. \begin{array}{l} a = \left| \dfrac{\cos(\psi + \zeta)}{\sin\psi} \right| l \\[6pt] b = \left| \dfrac{-\cos\zeta}{\sin\psi} \right| l \end{array} \right\} \quad (7)$$

by using a distance l between the transmitting sensor 9 and the receiving sensor 4, the incident angle $\zeta$ of an ultrasonic wave beam 11, and a scattering angle $\psi$. The time for the ultrasonic wave to propagate through points $(x_h, y_i)$, $(x_j, y_i)$ and $(x_h, y_k)$ is now denoted by $\tau_{yixjyk}$, where $h < j$ and $i < k$ stand so that the above three points lie on apices of a triangle. Further, it is assumed that the ultrasonic wave propagates over a distance between points $(x_m, y_n)$ and $(x_p, y_q)$ at a rate of $v_{xmynxpyq}$ and the reciprocal of the rate, namely, a time for propagation over a unit distance is denoted by $n_{xmynxpyq}$. In the above denotation, i, j, h, k, m, n, p and q are optional values.

Then, a propagation time $\tau_{011}$ over points $A_{00}$ (0, 0), $A_{10}$ (1, 0) and $A_{01}$ (0, 1) is, $$\left.\begin{array}{l} \tau_{011} = an_{0010} + bn_{1001} \\ \text{Similarly, propagation times over points } A_{00}, A_{20} \text{ and} \\ A_{02}, \text{ points } A_{00}, A_{30} \text{ and } A_{03}, - - - \text{ are} \\ \quad \tau_{022} = an_{0010} + an_{1020} + bn_{2011} + bn_{1102} \\ \quad \tau_{033} = an_{0010} + an_{1020} + an_{2030} \\ \quad \quad + bn_{3021} + bn_{2112} + bn_{1203} \\ \\ \text{Similarly, with the original at the point } A_{01}, \\ \text{propagation times over points } A_{01}, A_{11} \text{ and } A_{02}, \\ \text{points } A_{01}, A_{21} \text{ and } A_{03} - - - \text{ are} \\ \quad \tau_{112} = an_{0111} + bn_{1102} \\ \quad \tau_{123} = an_{0111} + an_{1121} + bn_{2112} + bn_{1203} \\ \\ \text{Similarly, with the original at the point } A_{02}, \\ \text{propagation times over points } A_{02}, A_{12} \text{ and } A_{03}, \\ - - - \text{ are} \\ \quad \tau_{213} = an_{0212} + bn_{1203} \\ \end{array}\right\} \quad (8)$$

Similar relationships are obtained with originals at points $A_{03}$, $A_{04}$, .... Assumption will now be made such that $n_{0010} = n_{1001} = n_{011}$ is held for a minimal unit of a triangle as defined by, for example, $A_{00}$ (0, 0), $A_{10}$ (1, 0) and $A_{01}$ (0, 1), and that $n_{0111} = n_{1102} = n_{012}$, $n_{1020} = n_{2011} = n_{121}$, $n_{0212} = n_{1203} = n_{023}$ ... are similarly held for the other minimal triangles as defined by $A_{01}$, $A_{11}$, and $A_{02}$, $A_{10}$, $A_{20}$ and $A_{11}$, $A_{02}$, $A_{12}$ and $A_{03}$ ... respectively. Thus, equation (8) can be simplified as follows.

$$\left.\begin{array}{l} \tau_{011} = (a + b) n_{011} \\ \tau_{022} = an_{011} + (a + b) n_{121} + bn_{012} \\ \tau_{033} = an_{011} + an_{121} + (a + b) n_{231} \\ \quad \quad + bn_{122} + bn_{013} \\ \\ \cdot \\ \cdot \\ \cdot \\ \tau_{112} = (a + b) n_{012} \\ \tau_{123} = an_{012} + (a + b) n_{122} + bn_{013} \\ \\ \cdot \\ \cdot \\ \tau_{213} = (a + b) n_{013} \end{array}\right\} \quad (9)$$

By measuring each time $\tau$, reciprocals of velocities of sound at respective sections can be obtained from equation (9) in sequence of $n_{011}$, $n_{012}$, $n_{013}$, $n_{121}$, $n_{122}$... and hence the sound velocity distribution can be obtained. By using the thus obtained sound velocity distribution, the stress distribution can be measured from equation (1) or (3).

As described above, according to the method of the present invention, the scattering point is used as the reference point to eliminate the necessity of information regarding the thickness of the body. In addition, the calculation of $L_{ij}$ required in the conventional method can also be eliminated, thus ensuring easy calculation for measurement of the velocity of sound.

The invention will now be described in more detail by way of example.

Figure 5:
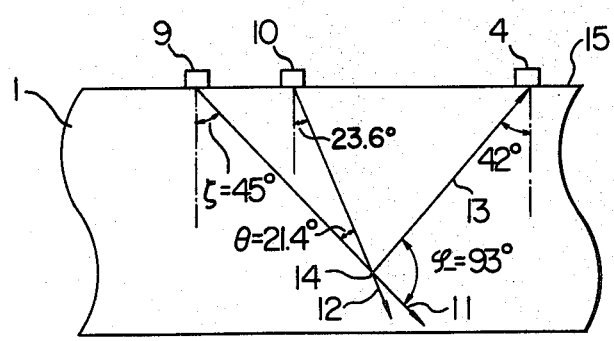
FIG. 5 is a diagrammatic representation showing the positional relation between sensors when the angle $\theta$ between incident ultrasonic wave beams is 81°.

The locations of the sensors are related to the propagation of the ultrasonic wave beams as shown in FIG. 5. A solid body 1 is made of iron, for example. An ultrasonic wave beam 11 is a longitudinal wave of 5 MHz and another ultrasonic wave beam 12 is a transversal wave of 3.0 MHz. Since $\omega_2/\omega_1$ is 0.6, an angle $\theta$ between there incident beams is 80.6° or 21.4° as obtained from the graph of FIG. 2. As a scattered wave 13, a component of a differential frequency of $\omega_- = 2$ MHz is preferentially used which propagates in a direction of $\psi_- = 93°$. The distance l between a transmitting sensor 9 and a receiving sensor 4 is 10 mm. Then, a and b in FIG. 4 are specified from equation (7) as 7.4 mm and 7.1 mm, respectively. Accordingly, the distance between another transmitting sensor 10 and the receiving sensor 4 is 7.1 mm. Another ultrasonic wave beam 12 is transmitted from the transmitting sensor 10 at an incident angle of 23.6°.

Figure 6:
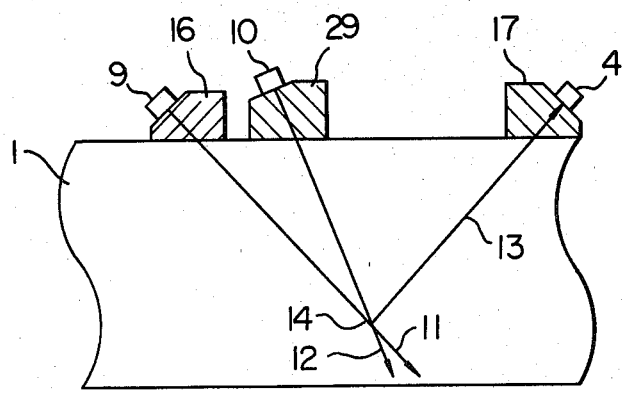
FIG. 6 is a diagrammatic representation showing one example of a shoe structure.

For transmission of the ultrasonic wave beams 11 and 12 and reception of the scattered wave 13 as illustrated in FIG. 5, shoes are constructed as shown in FIG. 6. The shoes are made of the same material as the body to be measured (iron in this embodiment). The transmitting sensors 9 and 10 and the receiving sensor 4 are fixed to the corresponding shoes through a suitable ultrasonic wave coupling material such as oil, water, glass or the like. When a shoe 16 is fixed and shoes 17 and 29 are caused to scan on the top surface of a body 1, the propagation distance of the ultrasonic wave is changed and the corresponding propagation time can be measured. The material for the shoe, exemplified as iron in this embodiment, is not limitative but may be replaced by another material such as, for example, acryl.

Figure 7:
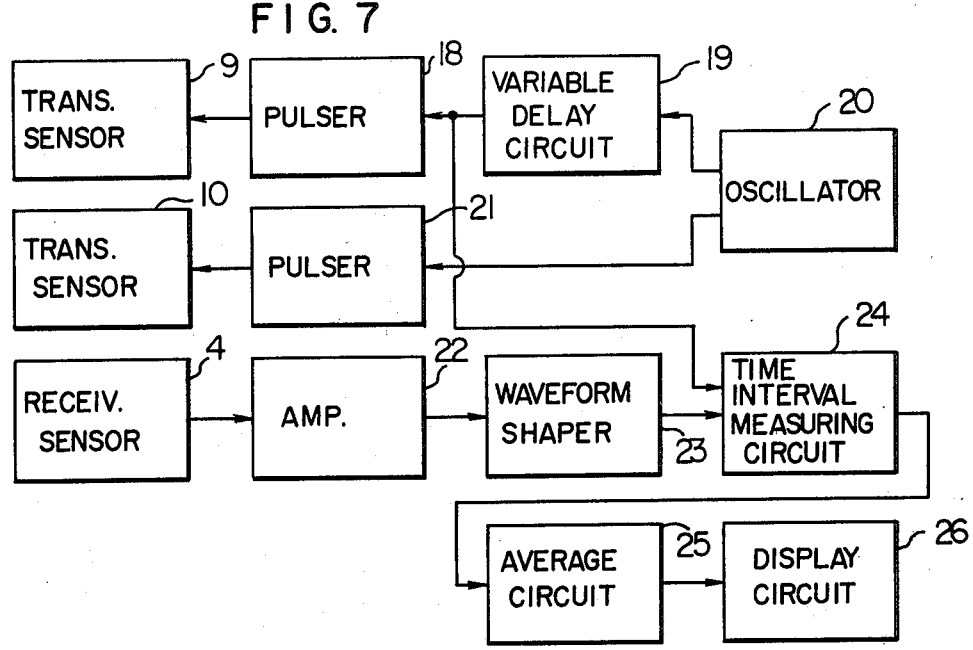
FIG. 7 is a block diagram of a measuring circuitry according to the invention.

FIG. 7 illustrates, in block form, an ultrasonic wave generator and receiver circuit and an ultrasonic wave propagation time measuring circuit. A transmitter or oscillator 20 sends pulses at a fixed interval, for example, 1 msec. The pulses are applied as a trigger signal to a pulser 18 via a variable delay circuit 19. This trigger signal causes a transmitting sensor 9 to emit a longitudinal wave of 5 MHz. The pulses from the oscillator 20 are also applied to a pulser 21 to cause a transmitting sensor 10 to emit a transversal wave of 3 MHz. Since the longitudinal wave propagates at a rate of 5940 m/s and the transversal wave at a rate of 3250 m/s in iron materials, the variable delay circuit 19 for adjustment of the emitting time of the longitudinal wave is provided to assure simultaneous arrival of both types of waves at the scattering point. Specifically, in this embodiment, the distance corresponding to a in FIG. 4 is 7.4 mm and the ultrasonic wave beam 12 travels a propagation distance of 5.7 mm before reaching the scattering point. Accordingly, the propagation times associated with the two types of wave are 1.25 μs and 1.75 μs and a delay time of 0.50 μs is required for obtaining the scattered wave at the point $A_{10}$ (1, 0) in FIG. 4.

The scattered wave from the scattering point is received by a receiving sensor 4, amplified at an amplifier to a suitable amplitude and fed to a waveform shaper 23. A time interval measuring circuit 24 is applied with the output pulses from the variable delay circuit 19 and triggered thereby to measure a time interval between the reception of the trigger pulse and the reception of the output of the waveform shaper 23. This time interval corresponds to $\tau$ shown in equation (9). Values of $\tau$ are fed to an average circuit 25. To improve accuracy of the measurement, the propagation time $\tau$ is measured 500 to 1000 times at each location. The averaged value is displayed by a display circuit 26. The average circuit 25 incorporates memories for storage of currently calculated values and measured values as well as data to be displayed at the display circuit. Optionally, the average circuit may be replaced by a computer.

The above measurement is repeated for locations along the y-axis shown in FIG. 4 to measure $\tau$ in equation (9). Specifically, the equation (9) is exactly adapted for i=3. Namely, $$\tau_{011} = (a+b) n_{011} \quad (10)$$
$$\tau_{022} = an_{011} + (a+b) n_{121} + bn_{012} \quad (11)$$
$$\tau_{033} = an_{011} + an_{121} + (a+b) n_{231} + bn_{122} + bn_{013} \quad (12)$$
$$\tau_{112} = (a+b) n_{012} \quad (13)$$
$$\tau_{123} = an_{012} + (a+b) n_{122} + bn_{013} \quad (14)$$
$$\tau_{213} = (a+b) n_{013} \quad (15)$$

From the above equations, the following equation (16)

$$\left. \begin{array}{l} n_{011} = \dfrac{\tau_{011}}{a+b} \\[6pt] n_{012} = \dfrac{\tau_{112}}{a+b} \\[6pt] n_{013} = \dfrac{\tau_{213}}{a+b} \\[6pt] n_{121} = \dfrac{(a+b)\tau_{022} - a\tau_{011} - b\tau_{112}}{(a+b)^2} \\[6pt] n_{122} = \dfrac{(a+b)\tau_{123} - a\tau_{112} - b\tau_{213}}{(a+b)^2} \\[6pt] n_{231} = \dfrac{(a+b)^3 \tau_{033} - ab\tau_{011} - a(a+b)\tau_{022} + 2ab\tau_{112} - b(a+b)\tau_{123} - ab\tau_{213}}{(a+b)^3} \end{array} \right\} \quad (16)$$

is obtained which determines values of n and consequently the velocity of sound is each cell. Thus, from equation (3), stress P in each cell and consequent stress distribution in the body can be measured.

Figure 8A:
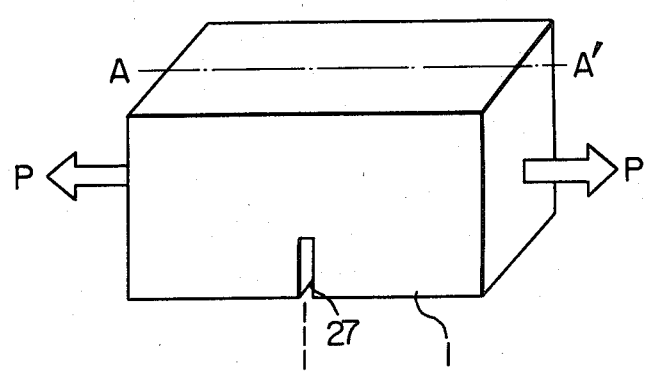
FIGS. 8a and 8b are diagrams useful in explaining stress distribution in a body with a cutting when it is applied with a fixed tension.
Figure 8B:
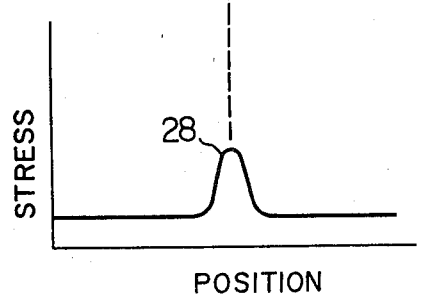

Referring to FIG. 8a, solid body with a cutting 27 as shown therein is subjected to a tension P to create stress distribution as shown in FIG. 8b on a sectional area taken along line A A'. It will be appreciated that the stress remains constant in the absence of the cutting 27 but a stress concentration is created corresponding to the presence of the cutting, resulting in an increased stress as shown at 28. The probes are then located on the line A—A' in an layout as explained with reference to FIG. 5, and the sound velocity distribution in the body and consequent stress distribution therein pursuant to equation (3) are measured.

In the foregoing embodiment, both the ultrasonic wave beams 11 and 12 are used in the form of pulses but one of the beams (for example, beam 12) may be a continuous wave. In such a modification, the variable delay circuit 19 may be eliminated and the pulser 21 may be replaced by a power amplifier for amplification of the continuous wave, with the remaining components unchanged. This modification advantageously eliminates the adjustment for the variable delay circuit.

The sensor in the foregoing embodiment is a probe of the type normally used in a method for ultrasonic detection of defects but may be an array type probe. In this case, the mechanical scanning of the sensor is not required but instead, positions for generation of the ultrasonic wave beams are electronically scanned. Such an electronic scanning advantageously improves accuracy of information regarding probe positions. Further, in accordance with the type of calculation processing, other coordinate systems than the oblique coordinate system may be used. Moreover, the approximation for equation (9) and handling of data therefor may be carried out in a different manner.

In place of the combination of the longitudinal and transversal incident waves for creation of the longitudinal scattered wave, two transversal incident waves may be combined to create a longitudinal scattered wave.

What is claimed is:

1. A method of measuring stress distribution comprising the steps of:

emitting two ultrasonic waves of different frequencies into a body under consideration from different locations on a surface of the body;

receiving a scattered wave created at a scattering point in the body by the interaction between the two ultrasonic waves;

causing the emitting locations of the ultrasonic waves and the receiving location of the scattered wave to scan; and measuring the stress distribution in the body on the basis of the received outputs resulting from the scanning.

* * * * *